United States Patent [19]

Savidge et al.

[11] 4,230,804
[45] Oct. 28, 1980

[54] WATER-INSOLUBLE PENICILLIN ACYLASE PREPARATION

[75] Inventors: Thomas A. Savidge, Stayning; Lawson W. Powell, Worthing, both of England

[73] Assignee: Beecham Group Limited, England

[21] Appl. No.: 955,224

[22] Filed: Oct. 27, 1978

Related U.S. Application Data

[60] Continuation of Ser. No. 832,343, Sep. 12, 1977, abandoned, which is a continuation of Ser. No. 709,009, Jul. 26, 1976, abandoned, which is a division of Ser. No. 532,051, Dec. 12, 1974, Pat. No. 4,001,264.

[30] Foreign Application Priority Data

Dec. 28, 1973 [GB] United Kingdom ............... 59978/73

[51] Int. Cl.$^2$ ................................................. C07G 7/02
[52] U.S. Cl. .................................. 435/180; 435/181; 435/231
[58] Field of Search ..................... 195/63, 68, DIG. 4; 435/180, 177, 231, 181

[56] References Cited

U.S. PATENT DOCUMENTS

| | | | |
|---|---|---|---|
| 3,705,084 | 12/1972 | Reynolds | 195/68 |
| 3,860,490 | 1/1975 | Guttag | 195/59 X |
| 3,871,964 | 3/1975 | Huper et al. | 195/63 |
| 3,883,394 | 5/1975 | Savidge et al. | 195/63 |
| 3,910,825 | 10/1975 | Huper et al. | 195/63 X |
| 3,983,001 | 9/1976 | Coupek et al. | 195/63 |

FOREIGN PATENT DOCUMENTS 2143062  3/1972  Fed. Rep. of Germany .

*Primary Examiner*—David M. Naff
*Attorney, Agent, or Firm*—Jacobs & Jacobs

[57] ABSTRACT

Novel re-usable water-insoluble penicillin acylase complexes are provided wherein a penicillin acylase is adsorbed on a water-insoluble polymer or co-polymer of methacrylic acid and cross-linked with a water-soluble aldehyde selected from the group consisting of glutaraldehyde, glyoxal and formaldehyde. The complexes are useful in the production of 6-APA from penicillins G and V.

6 Claims, No Drawings

WATER-INSOLUBLE PENICILLIN ACYLASE PREPARATION

This application is a continuation of application Ser. No. 832,343 filed Sept. 12, 1977 which is a continuation of application Ser. No. 709,009 filed July 26, 1976, both now abandoned, which is a division of application Ser. No. 532,051 filed Dec. 12, 1974, now U.S. Pat. No. 4,001,264.

This invention relates to improved enzyme complexes and particularly to those prepared from acylase enzymes known to split the amide bond of penicillins. Such enzymes are herein termed penicillin acylases and they are useful in producing 6-aminopenicillanic acid from penicillins obtained by fermentation processes of naturally-occurring materials, that is using the enzyme under such pH conditions that deacylation (or splitting of the amide group) of the pencillin occurs with the formation of the desired 6-aminopenicillanic acid. The invention also relates to the use of the improved acylase enzymes in the production of 6-aminopenicillanic acid (hereinafter called "6-APA").

While such penicillin acylase (or deacylase) enzymes in either cell-bound or cell-free states have been used for the stated purpose since about 1961, difficulties arise when using the cell-free enzyme because this is not readily separated from the reaction mixture; moreover the cell-bound water-soluble enzyme is not easily re-used. Furthermore, both types of enzyme produce 6-APA which is contaminated with trace amounts of bacterial protein. It has been proposed in British patent specification No. 1,193,918 to overcome these difficulties by bonding the enzyme to a polymer substrate and thereby rendering it water-insoluble. However, such polymer-enzyme complexes have been found to have a poor mechanical stability when the polymers employed as substrate are those generally available on a commercial scale for other purposes. These polymers have to be specially designed and prepared for this purpose and this is unduly expensive. Moreover, when 6-APA is prepared by the action of acylase enzymes it is necessary to control the pH of the reaction mixture within a narrow range throughout the reaction and this requires continual addition of an alkali to neutralise the carboxylic acid which results from the liberated penicillin side chain. It has been found that, when the acylase enzyme is directly bonded by a covalent linkage to a polymer substrate, care needs to be taken in the choice of the alkali used for such neutralisation and that usually the alkali of choice, sodium hydroxide, can not be used without the enzyme becoming rapidly denatured. Consequently if a volatile base such as ammonia or triethylamine has to be used, expensive modification of the plant presently in use for making 6-APA with the aid of the acylase enzyme in its unbound and water-soluble form, may be required, because with the unbound enzyme there is no difficulty in using sodium hydroxide for neutralisation of the liberated side chain acid.

It has also been proposed in the specification of German Offenlegungsschrift No. 2,143,062 to prepare a water-insoluble penicillin acylase preparation by adsorbing the acylase on a substrate and there cross-linking it by the action of a water-soluble dialdehyde with and without the formation of links between the polymer substrate and the enzyme. In this method the enzyme is mainly cross-linked around the substrate, rather than bonded thereto by covalent linkages. In the aforesaid specification various substrates are described; for example, anionic exchange resins, that is those containing basic groups such as primary, secondary or tertiary amino groups or similar nitrogenous functional groups; or carboxymethylcellulose; or polymers having a neutral reaction for example because the functional groups present are ester groups.

It has been discovered that substrates having negatively charged functional groups are superior to substrates having positively charged functional groups. For example, two experiments to compare cellulose having either positively or negatively charged groups, viz. diethylaminoethyl (DEAE) cellulose and carboxymethyl (CM) cellulose were carried out. The conditions for coupling penicillin acylase to each substrate were optimised and the same enzyme solution was used for coupling to each support using these optimum conditions. The activity of the final immobilised enzyme preparation represented 11% and 42% of the original total activity of the enzyme solution for the DEAE and CM celluloses respectively. The lower activities of the DEAE cellulose preparations were due to poor adsorption of the enzyme. When the experiment was repeated using a different enzyme solution, the results were 24% and 56% for the DEAE and CM celluloses respectively. However the enzyme complexes prepared from celluloses have poor mechanical stability, as has been reported by D. L. Regan, P. Dunnill and M. D. Lilly "Immobilized Enzyme Reaction Stability: Attrition of the Support Material" in Biotechnology and Bioengineering: Vol XVI Pages 333–343 (1974).

Furthermore those complexes prepared by the adsorption-crosslinking technique wherein the substrate is a polymer with a neutral activity have characteristics of reactivity and reusability that can also be regarded as unsatisfactory. For example the stability of penicillin acylase adsorbed and cross linked onto the neutral substrate, Amberlite XAD-7 determined by storing the immobilised enzyme preparation at a temperature of 37° C. was unsatisfactory since the activity fell by 66% after 14 days storage.

We have found that if the technique of the aforesaid Offenlegungsschrift is empolyed with polymers or copolymers of methacrylic acid, that is polymers having a carboxylic acid function of the aliphatic type, the resulting enzyme complexes are suprisingly superior in having a high enzyme activity which is sustained after repeated use in the production of 6-APA. Substrates consisting of macroporous or gel type polymers of styrene, acrylic acid or phenolformaldehyde with either sulphonic, phosphoric or carboxylic functional groups have been found to be markedly inferior to macroporous and gel polymers and copolymers of methacrylic acid. The very good stability of these preparations may also be demonstrated by the results of storage at 37° C. In one such experiment, the activity of an immobilised enzyme preparation made by adsorbing and cross-linking acylase onto a macroporous polymer of methacrylic acid sold under the trade name Amberlite IRC-50 lost only 5% of its initial activity after 14 days storage at 37° C.

Such enzyme complexes also possess an enhanced mechanical stability. This feature of mechanical stability is important in any stirred tank reactor because of the need to stir the reaction very vigorously in order to maintain a uniform pH value and minimise alkali degradation of penicillin. Furthermore, in the improved reactor systems now being developed, for example where the insoluble enzyme complex is retained within the reactor by means of a mesh of appropriate size and where upon completion of a reaction to produce 6-APA, the reaction medium is drained off, the insoluble enzyme preparation remains within the reactor ready for re-use. By this means the physical losses of enzyme normally experienced when the whole mixture is removed from the vessel and the insoluble enzyme preparation is recovered by filtration or centrifugation and is returned to the reaction vessel are minimised. In addition microbial contamination of the enzyme preparation during handling is obviated. However, the enzyme complex must not become mechanically degraded so that appreciable losses occur as a result of it passing through the retaining mesh. Furthermore as it has been shown by Regan, Dunnill and Lilly (loc. cit.) that the small particles resulting from attrition of aminoethyl cellulose to which β-galactosidase was attached have higher specific activities than the larger particles, the loss of such particles from the reactor is likely to result in a loss of total activity disproportionate to the weight of material lost.

In a second reactor system, which has been described in Belgium Pat. No. 782646, the insoluble enzyme preparation is retained within a column reactor through which substrate is circulated at a fast flow rate in order that the necessary pH adjustments can be carried out in a vessel separate from the insoluble enzyme preparation. The substrate must therefore have hydraulic properties such that it does not become mechanically degraded by the high pressures needed to maintain the fast flowing reaction mixture. Each of these reactor systems may be modified to function as continuous reactor systems and the problems of adequate mechanical stability with enzyme reactivity and reusability still remain.

A further advantage of using polymers and copolymers of methacrylic acid is that these resins are themselves of good mechanical stability. Thus when enzyme complexes formed from them have declined in activity to an unacceptable value after repeated reuse in a reactor, the resin may be regenerated by stripping off the remaining enzyme by treating with hot alkali. Fresh enzyme may then be attached to the same resin.

We have also found that, when the enzyme complexes are prepared by adsorption on the aforesaid methacrylic acid polymers and copolymers followed by cross-linking with certain cross-linking agents, the resulting water-insoluble enzyme complex can be used in the production of 6-APA without undue care being needed in the choice of the alkali needed to neutralise the liberated side chain acid. Thus we have found that, unlike the systems in which the enzyme is directly bonded to a polymer substrate by covalent linkages, sodium hydroxide can be used for this purpose as is presently customary in the use of the free water-soluble enzymes. Accordingly, modification of the evaporators in the existing plant to cope with volatile alkalis, as would be necessary if ammonia or triethylamine had to be used for neutralisation, is avoided.

U.S. Pat. No. 3,705,084 describes the adsorption of enzymes onto polymeric surfaces and their subsequent cross-linking into place. Polymers and copolymers of methacrylic acid are stated to be suitable for making such polymeric surfaces. The Patent however specifies that the polymeric surfaces must have adsorption promoting groups selected from nitrilo ($\equiv$N) acid amido ($-CONH_2$) and ureido ($-NHCONH_2$) groups, and thus before polymers and copolymers of methacrylic acid can be used according to this Patent, carboxyl groups on the polymer and copolymer must be converted to one of these specified adsorption promoting groups. Accordingly the polymers and copolymers of methacrylic acid used in the Patent may be distinguished from those of the present invention by the presence of these specific adsorption promoting groups. Further by specifying the presence of these specific adsorption groups the Patent suggests that modified polymers and copolymers of methacrylic acid form more useful enzyme complexes than the un-modified polymers and copolymers. The Patent therefore teaches away from our discovery that with acylase enzymes it is the un-modified polymers and copolymers of methacrylic acid which are to be preferred.

To demonstrate the superiority of polymers and copolymers of methacrylic acid in acylase enzyme complexes, acylase complexes were prepared from nylon and polyurethane, two polymers representative of the preferred and exemplified polymers of the U.S. patent, using glutaraldehyde as cross-linking agent, and their activity compared with an acylase enzyme complex prepared from Amberlite IRC-50 in a similar manner. When account was taken of differing particle size of the enzyme complexes, it was found that the Amberlite IRC-50 complex was two to three times more active than the polyurethane complex, and as much as eleven times more active than the nylon complex. These results are described in detail in the specific Examples later in the specification.

The concept of adsorbing an enzyme on a substrate and cross-linking it in situ, is also described in British patent specification No. 1,257,263. This does not however make any reference to penicillin acylase enzymes: nor does it describe the use of methacrylic acid polymers and copolymers as substrates: nor does it refer to the advantages that are obtained from choosing substrates of good mechanical stability. Nevertheless, it extends the concept of cross-linking the enzyme around the substrate by advocating the use of polyfunctional reagents other than water-soluble dialdehydes, for example by the use of bis-diazo-o-dianisidine. Similarly, we believe the concept of our invention can be extended to include glyoxal and formaldehyde as cross-linking agents, in addition to glutaraldehyde.

Accordingly, from one aspect the present invention provides a water-insoluble enzyme complex which comprises a penicillin acylase enzyme adsorbed on a water-insoluble polymer substrate and cross-linked with a cross-linking agent selected from glutaraldehyde, glyoxal and formaldehyde, the said polymer substrate being a water-insoluble polymer or copolymer of methacrylic acid.

From a second aspect, the invention provides a process for the preparation of a water-insoluble enzyme complex of the invention, which comprises adsorbing a penicillin acylase enzyme on a water-insoluble polymer or copolymer of methacrylic acid followed by treatment with a cross-linking agent selected from glutaraldehyde, glyoxal and formaldehyde.

From a third aspect, the invention also provides a process for the production of 6-aminopenicillanic acid, which comprises treating benzylpenicillin or phenoxymethylpenicillin or a salt thereof in aqueous solution at pH of from 6.0 to 9.0 with a water-insoluble enzyme complex according to the invention.

Preferably the acylase enzyme for present use is obtained from bacteria such as strains of *Escherichia coli*, when used for preparing 6-APA from benzylpenicillin; or for example, from fungi and actinomycetes when phenoxymethylpencillin is used as the starting material.

The enzymatic activity of the deacylase enzyme is conveniently determined in relation to its ability to produce 6-APA from benzylpenicillin. Thus the activity for the deacylase enzymes are herein recorded as the amount of 6-APA (given in micromoles $\mu M$) produced from a solution of benzylpenicillin at pH 7.8° and 37° C. per minute and per milligram of protein content of the enzyme, the protein content being assayed by the standard method of Lowry. The enzymatic activity of the enzyme complexes of the invention is similarly determined on the basis of the amount of 6-APA (in $\mu M$) produced from benzylpenicillin at pH 7.8° and 37° C. per minute but on the basis of the weight of the enzyme complex in grams.

We have found that both the efficiency of the adsorption cross-linking reaction and specific activity of the formed water-insoluble enzyme complex improve as the purity of the enzyme initially used increases. However, beyond a certain purity the improvements obtained for a given increase in purity decrease markedly, and so there is an economic limit to the purity of the enzyme that is desirable. Thus the purity of the deacylase enzyme is usually within the range of 0.15 to 50 micromoles/min/mg protein content and is conveniently within the range of 1.5 to 30 micromoles/min/mg protein.

It may thus be desirable to improve the purity of the enzyme before adsorption and cross-linking. This may be achieved by heating the enzyme solution at about 50° C. for a short period, e.g. about 30 minutes and/or by ultrafiltration. Other conventional methods of enzyme purification, e.g. fractional precipitation or treatment with ion-exhange celluloses or Sephadex, may also be used.

The substrate for present use are polymers or copolymers of methacrylic acid. They therefore contain free carboxylic groups which give the polymer an acidic function to a degree which seems about optimum for good adsorption of penicillin acylase enzymes without denaturation thereof. Macroporous polymers and copolymers of methacrylic acid are to be preferred to gel polymers and copolymers of methacrylic acid.

The methacrylic polymers are required to be water-insoluble and are therefore usually in the form of cross-linked copolymers, for example copolymers of methacrylic acid with divinylbenzene or a diester of a glycol with methacrylic acid, for example by the use of ethylene glycol bis-methacrylate. Other co-monomers, such as methacrylate esters may also have been used in the preparation of copolymers for present use. One advantage of the present invention is that it permits the use of polymer substrates that are already commercial products for other purposes, particularly as cationic exchange resins of a weakly acidic nature. Particularly suitable is the methacrylic acid/divinylbenzene copolymer sold under the trade name Amberlite IRC-50 by Rohm and Haas Co. of U.S.A. having an apparent wet density of 0.69 g/ml, a wet exchange capacity of 3.5 m.eq./ml and a B.S.S. mesh size of 14–52 and the methacrylic acid copolymer sold under the trade name Zeokarb 227 by the Permutit Co. Ltd. The last mentioned is a divinylbenzene/methacrylic acid copolymer which also contains some benzene sulphonyl groups.

The polymer substrates for present use are preferably in the form of finely-divided particles or beads of particle size such that they will pass a 100 A.S.T.M. sieve, i.e. of particle size diameter below 0.1 mm. However the resulting enzyme complex must not be so finely-divided that it cannot be separated from the reaction mixture by a mesh filtration process or used in a column reactor. Thus the polymer should have a particle size in excess of 0.01 mm., i.e. it should be substantially retained on a 800 A.S.T.M. sieve. The specific choice of particle size within this range will depend on the nature of the reactor system to be used.

The acylase enzyme to be contacted with the polymer should be an aqueous solution and have been dialysed until its ionic conductivity has been lowered from the usual value of 5–10 m.mhos to within the range of from 0.1 to 5 m.mhos, preferably about 1 m.mhos. The pH of the enzyme solution should desirably be between 4.5 and 7.0 and some empirical experiments may be necessary to determine the optimum pH value within this range if maximum adsorption and retained enzyme activity is to be achieved. However this optimum value is usually between pH 5.2 and 6.5. The polymer should be contacted with the enzyme solution for a sufficient period to ensure maximum emzyme adsorption: this residence time is usually between 2 and 16 hours.

After its adsorption on the substrate, the enzyme is cross-linked in situ by treatment with a cross-linking agent selected from glutaraldehyde, glyoxal and formaldehyde. The use of glutaraldehyde or glyoxal is preferred, glutaraldehyde especially resulting in enzyme complexes of most advantageous properties when used in the production of 6-APA. The cross-linking agent is normally used in aqueous solution at a concentration between 0.1 and 15% by weight, preferably 0.5 to 5.0% by weight.

After completion of the cross-linking reaction, it is desirable to ensure that any of the cross-linking agent that has not reacted is removed or rendered innocuous. For instance excess agent may be removed by washing with water or with a solution of an amine compound and we have found urea to be very effective for this purpose.

Before use in the production of 6-APA, the pH of the enzyme complex should be carefully adjusted to that to be used in said production process, usually by the addition of alkali at the end of the cross-linking reaction. Such pH is within the range of 6.0 to 9.0, but is usually between pH 7.0 and 8.5, a pH of 7.8 being preferred. For such use the enzyme complex of the invention is contacted with an aqueous solution of benzylpenicillin or phenoxymethylpenicillin or of a salt thereof, such solution having the desired pH. The reaction temperature is usually maintained within the range 30°–50° C., preferably 37° C. During the reaction phenylacetic acid is liberated from benzylpenicillin and phenoxyacetic acid from phenoxymethylpenicillin and this acid is neutralised continuously or intermittently to control the pH of the reaction mixture within the desired range. As stated above the choice of alkali for this neutralisation appears not to be critical. Thus sodium hydroxide solution is most conveniently used, though a volatile amine base, such as ammonia or triethylamine, can be used if desired.

The water-insoluble enzyme complexes of the invention are often sufficiently stable, both mechanically and biologically, that they can be used to enable at least 40 successive splittings of penicillin to be carried out in a batch reactor.

The invention is illustrated by the following Examples in which there was employed a partially purified preparation of acylase enzyme which had been prepared by releasing the enzyme from the cells of an acylase-producing strain of *Escherichia coli* NCIB 8734 by mechanical means in a homogeniser.

Cell debris were then removed by filtration after adjustment to pH 5.0 and the enzyme solution was further purified as necessary to produce the required range of specific activities (i.e. 1.5 to 30 micromoles/min/mg protein). The enzyme solution was then dialysed until it had a conductivity of approximately 1 m.mho.

EXAMPLE 1

Aliquots (20–25 or 50 g) of commercially available cationic and anionic ion-exchange resins as stated below were suspended in distilled water (c. 100–500 ml) and adjusted to pH values between 4.4 and 6.3 in the case of the cationic resins and to pH values between 6.5 and 9.0 in the case of the anionic resins by the addition of sodium hydroxide or hydrochloric acid with vigorous agitation. The resins were recovered by filtration, washed well with distilled water and were resuspended in a solution of partially purified penicillin acylase (60–100, 250 or 500 ml; specific activity, 3.85–6.75 $\mu$M/min/mg protein; conductivity <1 m.mho) The amount of enzyme challenged to the resin was varied between 71 and 308 $\mu$M/min/g of resin. Enzyme was allowed to adsorb with gentle agitation for c. 16 hours when the resins were recovered by filtration, resuspended in a solution of glutaraldehyde in water (100 ml, 0.825%–3.3% w/v) and allowed to react for c. 16 hours. The resulting enzyme-resin complexes were recovered, washed 3 times with distilled water, resuspended in water or 0.2 M phosphate buffer pH 7.8 and adjusted to pH 7.8, treated for 1 hour with an aqueous solution of urea (100 ml, 0.1 M, pH 7.8) and finally washed 3 times with distilled water.

Each enzyme complex so prepared was used to prepare 6-APA from benzylpenicillin under standard conditions at pH 7.8 and 37° C. The activities of the enzyme complexes are given in Table I. The activities refer to complexes prepared at the optimum pH for enzyme adsorption and retained enzyme activity.

The Bio-Rex and Chelex resins are commercial products of Bio-Rad Laboratories of California, U.S.A., the Lewatit resins are commercial products of Bayer A. G. German Federal Republic, the Zeokarb and Zerolit resins are commercial products of The Permutit Co. Ltd. and the Amberlite resins are commercial products of Rohm & Haas, Philadelphia, U.S.A. It will be noted that the advantages of the present invention are limited to the cases where the substrate is a polymer or copolymer of methacrylic acid.

TABLE I

| Experiment | Nature of matrix and functional groups in the resin | Resin | Physical form of the resin | Specific activity of enzyme resin complex at optimum pH | |
|---|---|---|---|---|---|
| | | | | $\mu$M/min/g damp wt. | $\mu$M/min/g dry wt. |
| a | Styrene-quaternary ammonium | Amberlite IRA-938 | Macroporous | 10.4 | 32.4 |
| b | Styrene-quaternary ammonium | Amberlite IRA-401 | Gel | nil | nil |
| c | Acrylate-quaternary ammonium | Amberlite IRA-458 | Gel | 4.71 | 10.1 |
| d | Polystyrene-polyamine | Lewatit MP62 | Macroporous | 15.1 | 30.7 |
| e | Styrene-polyamine | Amberlite IR-45 | Gel | nil | nil |
| f | Acrylate-polyamine | Amberlite IRA-68 | Gel | nil | nil |
| g | Styrene-SO$_3$H | Lewatit SP120 | Macroporous | 19.3 | 39.2 |
| h | Styrene-SO$_3$H | Lewatit S100 | Gel | nil | nil |
| i | Styrene-SO$_3$H | Zerolit 325 | Gel | nil | nil |
| j | Styrene-SO$_3$H | Amberlite IR-120 | Gel | nil | nil |
| k | Phenol-formaldehyde-SO$_3$H | Bio-Rex 40 | Gel | 4.01 | 8.3 |
| l | Styrene-SO$_3$H | bio-Rad AG/MP/50 | Macroporous | 9.9 | 19.8 |
| m | Styrene-PO$_3$H$_2$ | Bio-Rex 63 | Gel | nil | |
| n | Styrene-CH$_2$—N(CH$_2$—COOH)$_2$ | Chelex 100 | Gel | 7.16 | 30.1 △ |
| o | Methacrylate-COOH | Amberlite IRC-50 | Macroporous | 37.0 | 88.8 |
| p | Acrylate-COOH | Amberlite IRC-72 | Macroporous | ca. 8.0 | ca. 24.0 △ |
| q | Acrylate-COOH | Amberlite IRC-84 | Gel | 7.0 | 13.9 |
| r | Acrylate-COOH | Zerolit 236 | Gel | ca. 8.0 | ca. 46.5 △ |
| s | + △ —COOH | Lewatit CHP-80 | Macroporous | 15.2 | 36.5 |
| t | + △ —COOH | Lewatit CHP | Macroporous | nil | nil |
| u | Phenol-formaldehyde —OH —COOH tr —COOH △ | Zerolit 216 | Gel | nil | nil |
| v | Polymethacrylate | Zeokarb | Gel | 25.9 | 57.0 |

TABLE I-continued

| Experiment | Nature of matrix and functional groups in the resin | Resin | Physical form of the resin | Specific activity of enzyme resin complex at optimum pH | |
|---|---|---|---|---|---|
| | | | | μM/min/g damp wt. | μM/min/g dry wt. |
| | —SO$_3$H | 227 | | | |

Notes:
△ Results very variable, quoted values are mean of several determinations.
△ Polymer structure not known.
△ Resin not available commercially.
△ Mesh size 100-200 cf. 14.50 of other resins.
Resins a-c are strongly anionic.
Resins d-f are weakly anionic.
Resins g-l are strongly cationic.
Resins o-u are weakly cationic.

EXAMPLES 2-5

These examples illustrate the effect of varying the purity of the acylase enzyme during the adsorption step. The procedure used was as described in Example 1. The enzyme was adsorbed at pH 5.7 and the enzyme-resin complex was treated with 3.3% w/v glutaraldehyde. The resin employed was 'Amberlite' IRC-50, which had been washed with alkali and then with acid. The specific activities of the enzyme complexes so obtained are as given in Table II below. The results of Table II indicate that increasing the purity of the initial enzyme within this range increases the specific activity of the enzyme complex.

TABLE II

| Example | Specific activity of the initial enzyme μM/min/mg protein | Enzyme activity challenged μM/min/g resin | Specific activity of the enzyme resin μM/min/g dry wt. |
|---|---|---|---|
| 2 | 4.64 | 216 | 38.1 |
| 3 | 7.87 | 463 | 72.0 |
| 4 | 20.5 | 1160 | 124.0 |
| 5 | 18.2 | 586 | 109.0 |

EXAMPLE 6-15

The importance of the pH at which the enzyme was adsorbed to the resin was demonstrated in these examples wherein:

(a) Five aliquots of 'Amberlite' IRC-50 resin (50 g) were adjusted to pH 4.9, 5.1, 5.3, 5.5 and 5.7 respectively, dried and then each was added to a solution of partially-purified penicillin acylase, (95 ml; activity, 60.9 μM/min/ml, 16.8 mg protein/ml; conductivity, 0.55 m.mhos; made up to a final volume of 200 ml). After adsorption for 16 hours the enzyme complex was treated in the manner described in Example 1; or (b) Five further aliquots of the same resin were treated in the same manner except that the adsorption process was carried out in the pH range 5.7-6.5. The enzyme used for these resins had the following characteristics (105 ml; activity, 54.7 μM/min/ml; 9.03 mg protein/ml; conductivity, 0.75 m.mhos).

The results of these experiments are given in Table III below. These results show that the optimum pH for the adsorption step is from pH 5.2 to 5.8.

TABLE III

| Example | pH | Specific activity of the enzyme complex μM/min/g dry weight |
|---|---|---|
| 6 | 4.9 | 30.2 |
| 7 | 5.1 | 21.2 |
| 8 | 5.3 | 40.8 |
| 9 | 5.5 | 49.0 |

TABLE III-continued

| Example | pH | Specific activity of the enzyme complex μM/min/g dry weight |
|---|---|---|
| 10 | 5.7 | 57.2 |
| 11 | 5.7 | 44.4 |
| 12 | 5.9 | 13.0 |
| 13 | 6.1 | 8.4 |
| 14 | 6.3 | 5.6 |
| 15 | 6.5 | 5.6 |

EXAMPLES 16 and 17

These examples illustrate the effect of using the same resin but differing in particle size. Thus there was used a chromatographic grade of the resin Amberlite IRC-50 i.e. Amberlite CG-50 Type I having a particle size passing a 100 A.S.T.M. sieve but retained on a 200 A.S.T.M. sieve (i.e. a particle size 0.074–0.149 mm).

An aliquot (15 g) of resin was allowed to adsorb enzyme (200 ml, 23.7 μM/min/ml; 3.86 μM/min/mg of protein) at pH 6.3 for 3 hours. The enzyme complex was recovered, treated with glutaraldehyde (200 ml, 0.825% w/v) for 16 hours and recovered and washed as described in Example 1. The product (21 g) had an activity of 114.5 μM/min/g damp wt. and this has to be compared with that in Example 2 wherein Amberlite IRC-50 was used of particle size passing a 14 A.S.T.M. sieve but retained on a 50 A.S.T.M. sieve (i.e. having a particle size diameter of 0.297–1.41 mm). This shows that improved results are obtained when the resin is of the smaller size.

The experiment was repeated using a Pharmaceutical grade of Amberlite, viz. Amberlite IRP-64 having a particle size passing a 100 A.S.T.M. sieve but being retained on a 500 A.S.T.M. sieve i.e. a particle size of <0.037–0.149 mm diameter. The resin was allowed to adsorb enzyme (3920 μM/min/g resin; specific activity, 17.4 μM/min/mg protein) at pH 6.3. The enzyme complex was then reacted with glutaraldehyde (3.3% w/v) and treated as described in Example 1. The resulting enzyme-resin complex had a specific activity of 478.4 μM/min/g damp weight.

EXAMPLE 18

The pH of Amberlite IRC-50 resin was adjusted to 5.5 either by washing with 0.2 M phosphate buffer of that pH or by slurrying in distilled water and adding sodium hydroxide solution. The resin was then further washed with this buffer solution until no change in the conductivity of the buffer could be noted.

The damp resin (100 g) was added to the pencillin acylase of activity 5.25 μM/min/mg protein in 500 ml of 0.02 M phosphate buffer of pH 5.5 and stirred for 20 hours at room temperature. The solid was recovered by filtration, re-suspended in 500 ml of 0.25% w/v glutaraldehyde dissolved in the phosphate solution and stirred for a further 20 hours at room temperature. The resulting enzyme complex was then recovered by filtration and washed with 0.2 M phosphate buffer solution of pH 7.8 until the resin was equilibrated at this pH.

The enzyme complex so prepared (15 g) was then used to split 200 ml of a 6.25% w/v aqueous solution of benzylpenicillin 0.02 M phosphate buffer at pH 7.8 for 2 hours at 37° C. It was found that the enzyme complex could readily be recovered for re-use and that its mechanical and biological stabilities were each retained such that the complex could be re-used at least 25 times.

EXAMPLE 19

This illustrates the use of an enzyme complex of the invention in a large scale production of 6-APA and the outstanding re-usability of the complex under these conditions.

An enzyme complex was prepared using 'Amberlite' IRC-50. It had an activity of 26.3 $\mu$M/min/g and was used to split 40 liters of benzylpenicillin solution of concentration 6.5% w/v made up in 0.02 M phosphate buffer. The enzyme complex was retained in the vessel by means of a wire screen. Thus at the completion of a reaction the solution of 6-APA product was filtered off, the complex washed with water and a further reaction was set in progress. The average efficiency of conversion to 6-APA of 50 successive reuses each of 6 hours duration was 95%.

EXAMPLE 20

This example illustrates the mechanical stability of an enzyme complex of the invention prepared and described in Example 1 from the resin Amberlite IRC-50 as compared to one prepared in similar fashion but from a polymer substrate of neutral activity, namely the resin XAD-7 which is a cross-linked acrylate ester commercially available from Rohm & Haas Corp. U.S.A.

Samples of each enzyme complex (1.6 kg) were suspended in 8 liters of 0.2 M phosphate buffer at pH 7.8 and 37° C. and each mixture was stirred for 72 hours at 200 r.p.m. in a New Brunswick Magnaferm fermenter with baffles. Samples were taken at 4 hourly intervals and visually inspected for breakdown of resin beads. Breakdown of the XAD-7 beads was significantly greater than those of the IRC-50 beads such that a sample of the latter at 64 hours resembled a sample of XAD-7 resin taken after 8 hours. These results clearly demonstrated the greater mechanical strength of the IRC-50 resin.

EXAMPLE 21

Amberlite IRC-50 (235 g, 39.4 $\mu$M/min/g) prepared as described in Example 1 was used to split 6.25% w/v potassium benzylpenicillin G in a series of ten consecutive experiments. Each experiment was carried out using 1 liter of potassium benzylpenicillin G for 2½ hours at 37° C. and at pH 7.8. The Amberlite IRC-50 was removed by filtration after each experiment and washed with distilled water. The filtrate and washings were concentrated by rotary vacuum evaporation, the concentrate mixed with an equal volume of methyl isobutyl ketone, cooled to 4°-10° C. and finally acidified to precipitate 6-aminopenicillanic acid. The 6-aminopenicillanic acid was washed with a little distilled water, rinsed with acetone and oven dried. The average weight yield of 6-aminopenicillanic acid from the ten experiments was 91.3%.

EXAMPLE 22

Adsorption of acylase enzyme to urethane coated polyethylene

Low density polyethylene particles (<400 $\mu$m) were coated with a urethane polymer (Urithane 641 W, Cray Valley Products Limited) and allowed to dry for 10 days. The material was then washed for 1 hour with 20% aqueous acetone (v/v), rinsed extensively with distilled water and aliquots (5 g) were allowed to adsorb enzyme (125 ml, 54.0 $\mu$M/min/ml, 3.80 $\mu$M/min/mg of protein) for 5 hours in the range pH 4.8–9.0. The urethane-coated particles were removed by filtration, treated with glutaraldehyde (75 ml, 3.3% w/v) for 3 hours and then equilibrated to pH 7.8 as described in Example 1.

Despite the urethane-coated particles having on average a smaller size than IRC-50, the specific activities obtained were 2-3 times less than those obtained using IRC-50.

| pH | Act. damp wt. $\mu$M/min/g |
|---|---|
| 4.8 | 11.3 |
| 5.2 | 14.0 |
| 5.6 | 16.4 |
| 6.0 | 13.2 |
| 6.4 | 13.6 |
| 7.0 | 12.3 |
| 7.5 | 7.8 |
| 8.0 | 10.0 |
| 8.5 | 9.0 |
| 9.0 | 12.2 |

EXAMPLE 23

Adsorption of acylase enzyme to nylon

Orgolacq (powdered nylon 6, diameter <30 $\mu$M, Ato Chimie (U.K.) Limited) was washed for 1 hour with 65% (w/v) formic acid and then rinsed extensively with distilled water. Aliquots (10 g) were allowed to adsorb enzyme (100 ml, 50.9 $\mu$M/min/ml, 4.7. $\mu$M/min/mg of protein) for 16 hours in the range pH 4.8–9.0. The powdered nylon was removed by filtration, treated with glutaraldehyde (100 ml, 3,3% w/v) for 3 hours and recovered and washed as described in Example 1. The highest activity obtained (pH 4.8) was 41.7 $\mu$M/min/g damp weight which was comparable with a typical preparation of IRC-50. However, when account was taken of the difference in particle size of the nylon and IRC-50, IRC-50 was seen to be far superior. Thus IRP 64 (Pharmaceutical Grade IRC-50, particle size 37-149 $\mu$M) could be coupled with acylase to give preparations of specific activity 478 $\mu$M/min/g damp weight, more than eleven times greater than the nylon preparations.

| pH | Act. damp wt. $\mu$M/min/g |
|---|---|
| 4.8 | 41.7 |
| 5.2 | 36.1 |
| 5.6 | 26.9 |
| 6.0 | 22.2 |
| 6.4 | 15.7 |
| 7.0 | 17.6 |
| 7.5 | 17.6 |
| 8.0 | 21.3 |

-continued

| pH | Act. damp wt. µM/min/g |
|---|---|
| 8.5 | 15.7 |
| 9.0 | 9.3 |

We claim:

1. A re-usable water-insoluble penicillin acylase complex wherein penicillin acylase is adsorbed on a methacrylic acid-divinyl benzene macroporous copolymer cationic exchange resin having a substantial proportion of carboxylic acid groups in free acid or anionic form and the adsorbed penicillin acylase is cross linked with a water-soluble aldehyde selected from the group consisting of glutaraldehyde, glyoxal and formaldehyde.

2. A complex according to claim 1 wherein the purity of the pencillin acylase is 1.5 to 30 micromoles/min/mg protein.

3. A complex according to claim 1 wherein the benzene of divinyl benzene in the copolymer also contains a proportion of benzene sulphonyl groups.

4. A complex according to claim 1 wherein the copolymer is in the form of finely-divided particles or beads of particle size 0.7 to 0.01 mm.

5. A complex according to claim 4 wherein the copolymer has the following characteristics:
apparent wet density 0.69 g/ml; wet exchange capacity 3.5 meq/ml and a particle size greater than 0.01 mm and retained on a 800 A.S.T.M. sieve.

6. A complex according to claim 1 wherein the aldehyde is glutaraldehyde.

* * * * *